United States Patent
Zhang

(10) Patent No.: US 10,973,522 B2
(45) Date of Patent: Apr. 13, 2021

(54) CIRCULAR STAPLER WITH TISSUE GAP INDICATOR ASSEMBLY

(71) Applicant: Covidien LP, Mansfield, MA (US)

(72) Inventor: Xiliang Zhang, Shanghai (CN)

(73) Assignee: Covidien LP, Mansfield, MA (US)

( * ) Notice: Subject to any disclaimer, the term of this patent is extended or adjusted under 35 U.S.C. 154(b) by 413 days.

(21) Appl. No.: 15/767,288

(22) PCT Filed: Oct. 20, 2015

(86) PCT No.: PCT/CN2015/092271
§ 371 (c)(1),
(2) Date: Apr. 10, 2018

(87) PCT Pub. No.: WO2017/066918
PCT Pub. Date: Apr. 27, 2017

(65) Prior Publication Data
US 2020/0237375 A1    Jul. 30, 2020

(51) Int. Cl.
*A61B 17/115* (2006.01)
(52) U.S. Cl.
CPC .............................. *A61B 17/1155* (2013.01)
(58) Field of Classification Search
CPC .............. A61B 17/115; A61B 17/1155; A61B 2090/0807; A61B 2090/0811; A61B 2017/00367
USPC ..................................................... 227/175.1
See application file for complete search history.

(56) References Cited

U.S. PATENT DOCUMENTS

| | | | |
|---|---|---|---|
| 3,193,165 | A | 7/1965 | Akhalaya et al. |
| 3,388,847 | A | 6/1968 | Kasulin et al. |
| 3,552,626 | A | 1/1971 | Astafiev et al. |
| 3,638,652 | A | 2/1972 | Kelley |
| 3,771,526 | A | 11/1973 | Rudie |
| 4,198,982 | A | 4/1980 | Fortner et al. |
| 4,207,898 | A | 6/1980 | Becht |
| 4,289,133 | A | 9/1981 | Rothfuss |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

Chinese Office Action issued in Chinese Application No. 201580083931.5, dated Apr. 8, 2020.

(Continued)

*Primary Examiner* — Anna K Kinsaul
*Assistant Examiner* — Veronica Martin

(57) ABSTRACT

A surgical stapler includes a handle assembly, a central body extending distally from the handle assembly, an anvil assembly and a cartridge assembly. The handle assembly includes a stationary handle defining a window and a tissue gap indicator assembly that includes a slide that supports indicia that is visible through the window. The indicator assembly includes a lever which couples the slide to a drive screw of the surgical stapler to translate movement of the drive screw into movement of the slide. The lever is configured and adapted to translate movement of the drive screw over a distance of X1 into movement of the slide over a distance of X2, wherein X2 is greater than X1.

18 Claims, 7 Drawing Sheets

(56) References Cited

U.S. PATENT DOCUMENTS

| | | |
|---|---|---|
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |

(56) References Cited

U.S. PATENT DOCUMENTS

| | | |
|---|---|---|
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 * | 12/2007 | Milliman ............ A61B 17/115 227/175.1 |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |

(56) References Cited

U.S. PATENT DOCUMENTS

| | | | |
|---|---|---|---|
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 * | 2/2012 | Milliman | A61B 17/115 227/175.1 |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 2003/0111507 A1 | 6/2003 | Nunez |
| 2004/0073090 A1 | 4/2004 | Butler et al. |
| 2005/0023325 A1 * | 2/2005 | Gresham | A61B 17/115 227/176.1 |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0230170 A1 * | 9/2009 | Milliman | A61B 17/0684 227/176.1 |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0051669 A1 * | 3/2010 | Milliman | A61B 17/115 227/175.2 |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |

(56) References Cited

U.S. PATENT DOCUMENTS

| | | |
|---|---|---|
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0172929 A1 | 7/2013 | Hess et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1* | 7/2013 | Mandakolathur Vasudevan ......... A61B 17/1155 227/175.2 |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |

FOREIGN PATENT DOCUMENTS

| | | |
|---|---|---|
| CN | 101330877 A | 12/2008 |
| CN | 103140179 A | 6/2013 |
| CN | 103800043 A | 5/2014 |
| CN | 104023653 A | 9/2014 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 2792308 A2 | 10/2014 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2005037084 A2 | 4/2005 |
| WO | 2008107918 A1 | 9/2008 |

OTHER PUBLICATIONS

European Search Report dated Jun. 11, 2019, issued in EP Appln. No. 15906437.

* cited by examiner

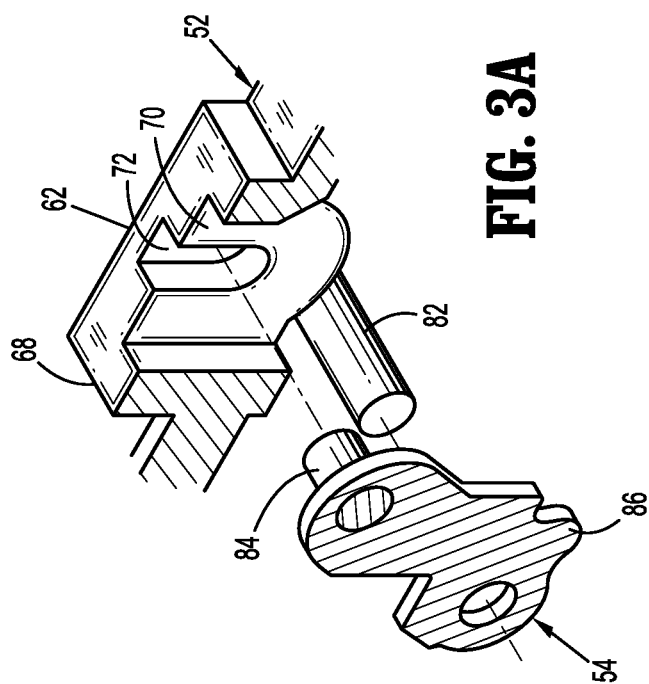
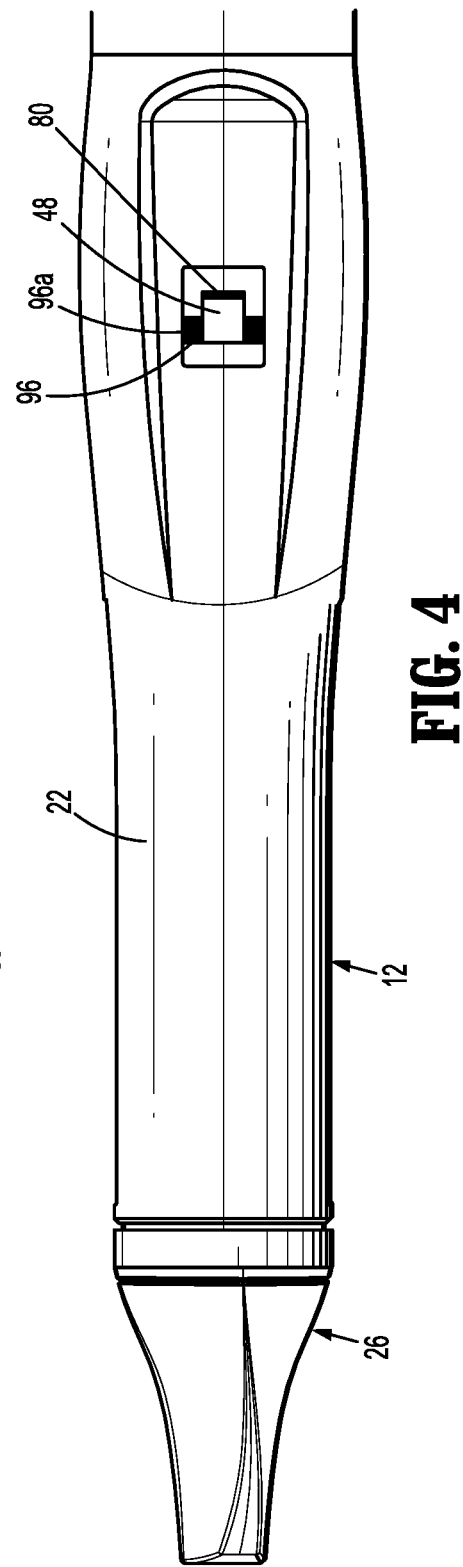

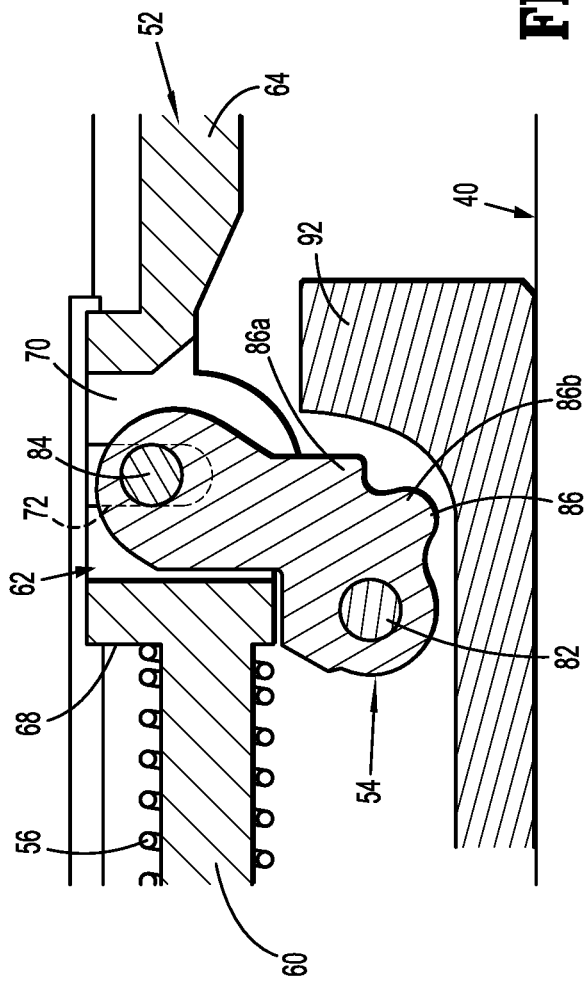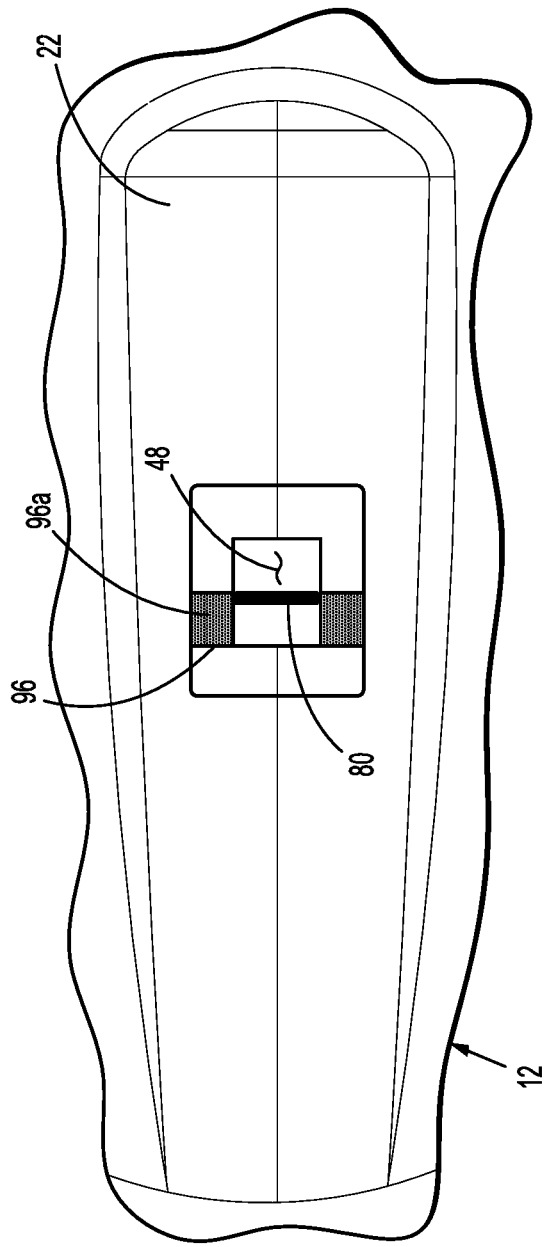

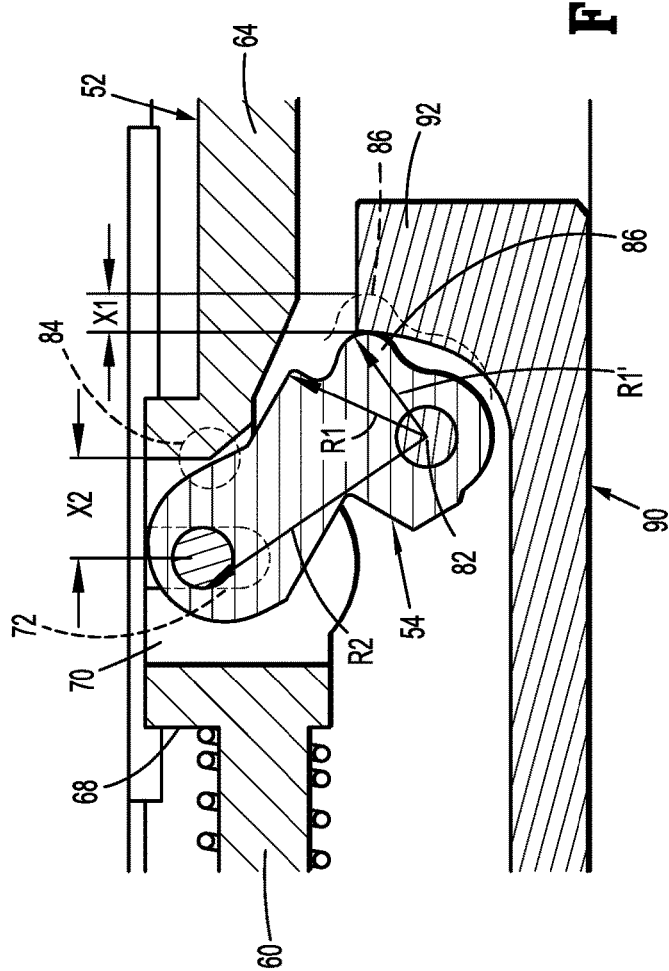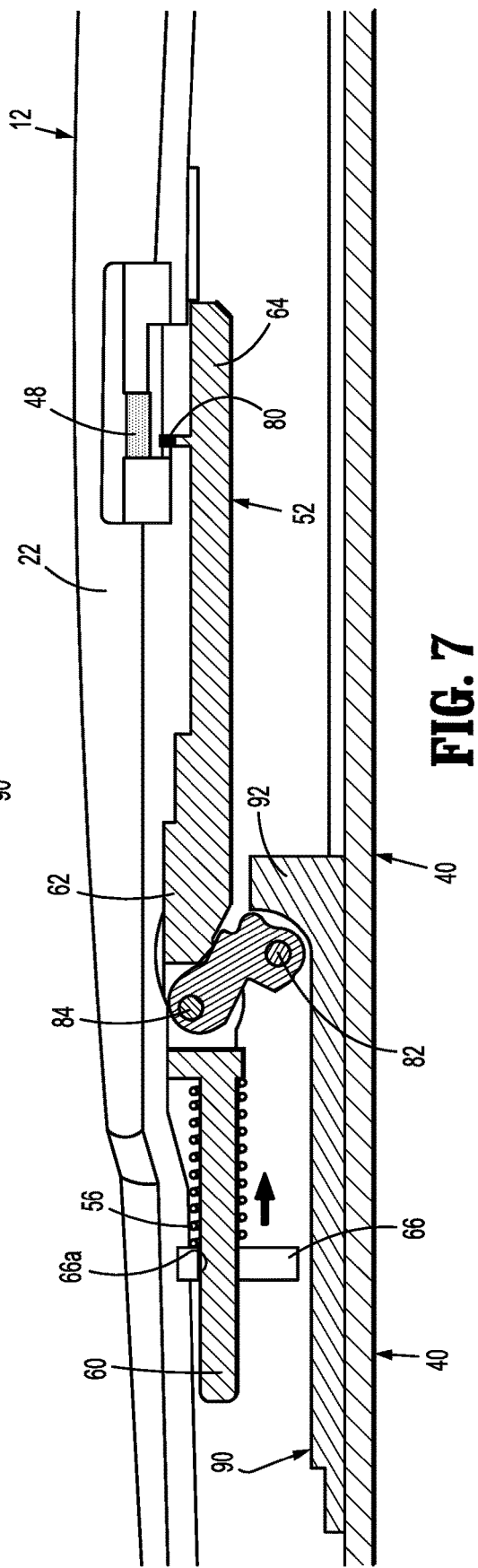

CIRCULAR STAPLER WITH TISSUE GAP INDICATOR ASSEMBLY

CROSS-REFERENCE TO RELATED APPLICATIONS

This application is a U.S. National Stage Application filed under 35 U.S.C. § 371(a) which claims the benefit of and priority to International Patent Application Serial No. PCT/CN2015/092271, filed Oct. 20, 2015, the entire disclosure of which is incorporated by reference herein.

BACKGROUND

1. Technical Field

The present disclosure relates to surgical staplers, and more particularly, to circular staplers including tissue gap indicator assemblies.

2. Background of Related Art

Anastomosis is the surgical joining of separate hollow organ sections. In known circular anastomosis procedures, two ends of organ sections are joined by means of a surgical stapler which drives a circular array of staples through each organ section and simultaneously cores any tissue interior of the driven circular array of staples to free a tubular passage. Examples of such devices are described in U.S. Pat. Nos. 7,234,624, 6,945,444, 6,053,390, 5,568,579, 5,119,983, 4,646,745, 4,576,167, and 4,473,077, the content of each of which is incorporated herein by reference in its entirety.

Typically, a circular stapling device has an elongated shaft having a handle portion at a proximal end and a staple cartridge at a distal end. An anvil assembly including an anvil rod with an attached anvil head is mounted to the distal end of the device. The anvil is approximated to clamp tissue between a staple holding component of the staple cartridge and an anvil plate of the anvil assembly. The clamped tissue is stapled by actuation of the handle portion to drive circular arrays of staples through the clamped tissue. Concurrently, an annular knife is advanced by actuation of the handle portion to core tissue inboard of the staple arrays.

Circular stapling devices that have tissue gap indicator assemblies for providing a visual indication of the size of the gap defined between the staple holding component of the staple cartridge and the anvil plate of the anvil assembly are conventional. In such devices, the indicator assembly typically identifies to a clinician when the staple cartridge and the anvil assembly have been approximated within a fire-ready zone, i.e., the zone in which the cartridge assembly and anvil assembly have been approximated sufficiently to allow for the proper formation of staples. Because of the small size of the staples being ejected and thus, the small range of tissue gaps that allow for proper staple formation, visualization of the degree of approximation within the fire-ready zone by a clinician is limited.

It would be advantageous to provide an improved tissue indicator assembly that allows for better visualization of the tissue gap size as the anvil and cartridge assemblies are approximated within the fire-ready zone.

SUMMARY

The present disclosure in one aspect is directed to a surgical stapler including a handle assembly having a stationary handle defining a window and a firing trigger. A central body extends distally from the handle assembly and a cartridge assembly is supported on a distal end of the central body. An anvil assembly is supported adjacent the distal end of the central body and is movable in relation to the cartridge assembly between spaced and approximated positions. An approximation mechanism includes a longitudinally movable drive screw that is operatively connected to the anvil assembly such that longitudinal movement of the drive screw effects movement of the anvil assembly in relation to the cartridge assembly between the spaced and approximated positions. The drive screw supports an abutment. An indicator assembly includes a slide and a lever. The slide has indicia visible through the window in the stationary handle. The lever is operatively engaged with the slide and positioned to engage the abutment on the drive screw when the drive screw is moved proximally within the stationary handle to translate longitudinal movement of the drive screw into longitudinal movement of the slide and to effect longitudinal movement of the indicia within the window. The lever is engaged with the abutment and the slide and is configured to translate movement of the abutment over a distance of X1 into movement of the slide over a distance of X2, wherein X2 is greater than X1.

In embodiments, the indicator assembly further includes a biasing member positioned to urge the slide distally within the stationary handle.

In some embodiments, the lever is pivotally mounted within the stationary housing about a post defining a pivot axis and includes an engagement surface positioned to engage the abutment that is spaced from the pivot axis of the post by a distance of R1.

In certain embodiments, the lever includes a protrusion that is operatively engaged with the slide and is spaced from the pivot axis defined by the post by a distance of R2, wherein R2 is greater than R1.

In embodiments, the engagement surface of the lever includes a first engagement member and a second engagement member. The first engagement member is spaced from the pivot axis defined by the post the distance R1 and the second engagement member is spaced from the pivot axis defined by the post a distance R1', wherein the R1' is greater than R1 but less than R2.

In some embodiments, the abutment defines a curved abutment surface.

In certain embodiments, the slide has a proximal portion, a central portion, and a distal portion and the central portion defines a channel that receives the lever.

In embodiments, the central portion of the slide defines a vertical groove and the lever includes a protrusion received within the vertical groove. The protrusion is movable within the vertical groove to facilitate longitudinal movement of the slide when the lever is pivoted.

In some embodiments, the biasing member is positioned about the proximal portion of the slide.

In certain embodiments, the indicia is formed on the distal portion of the slide.

In embodiments, the indicia includes a colored line.

In embodiments, the stationary handle defines second indicia positioned about the window, the second indicia being associated with the indicia on the slide to identify to a clinician when the cartridge and anvil assemblies are approximated into a fire-ready zone.

In some embodiments, the approximation mechanism includes a rotation knob that is rotatable in relation to the stationary handle to effect longitudinal movement of the drive screw within the stationary handle.

In certain embodiments, the indicator assembly includes a non-rigid link having a first end attached to a distal end of the lever and a second end attached to a proximal end of the slide.

In embodiments, the link is supported on a support post positioned between the distal end of the lever and the proximal end of the slide.

In some embodiments, the lever is pivotally mounted within the stationary handle about a post defining a pivot axis and includes a proximal end defining an engagement surface. The post is positioned between the proximal and distal ends of the lever. The engagement surface is positioned a distance of R1 from the pivot axis of the post and the distal end of the lever that is attached to the non-rigid link is positioned a distance of R2 from the pivot axis of the post, wherein R2 is greater than R1.

BRIEF DESCRIPTION OF THE DRAWINGS

Various embodiments of a surgical stapler including the presently disclosed tissue gap indicator assembly are described herein below with reference to the drawings, wherein:

FIG. 3A is a side perspective, cross-sectional, cutaway view of the indicator lever and indicator slide of the indicator assembly shown in FIG. 3;

FIG. 4 is a top view of the stationary handle of the surgical stapler shown in FIG. 1 illustrating the surgical stapler prior to approximation of the cartridge and anvil assemblies into a fire-ready zone;

FIG. 4A is a side cross-sectional, cutaway view of the indicator lever and indicator slide of the indicator assembly shown in FIG. 3 prior to approximation of the cartridge and anvil assemblies into a fire-ready zone;

FIG. 5 is a top view of the stationary handle of the surgical stapler shown in FIG. 1 illustrating the surgical stapler in a maximum tissue gap position of the fire-ready zone;

FIG. 6A is a side cross-sectional, cutaway view of the indicator lever and indicator slide of the indicator assembly shown in FIG. 3 after approximation of the cartridge and anvil assemblies into the minimum tissue gap position of the fire-ready zone;

FIG. 7 is a side cross-sectional view of the stationary handle of the surgical stapler shown in FIG. 1 as the indictor slide is returned to a unactuated position.

DETAILED DESCRIPTION OF EMBODIMENTS

Figure 1:
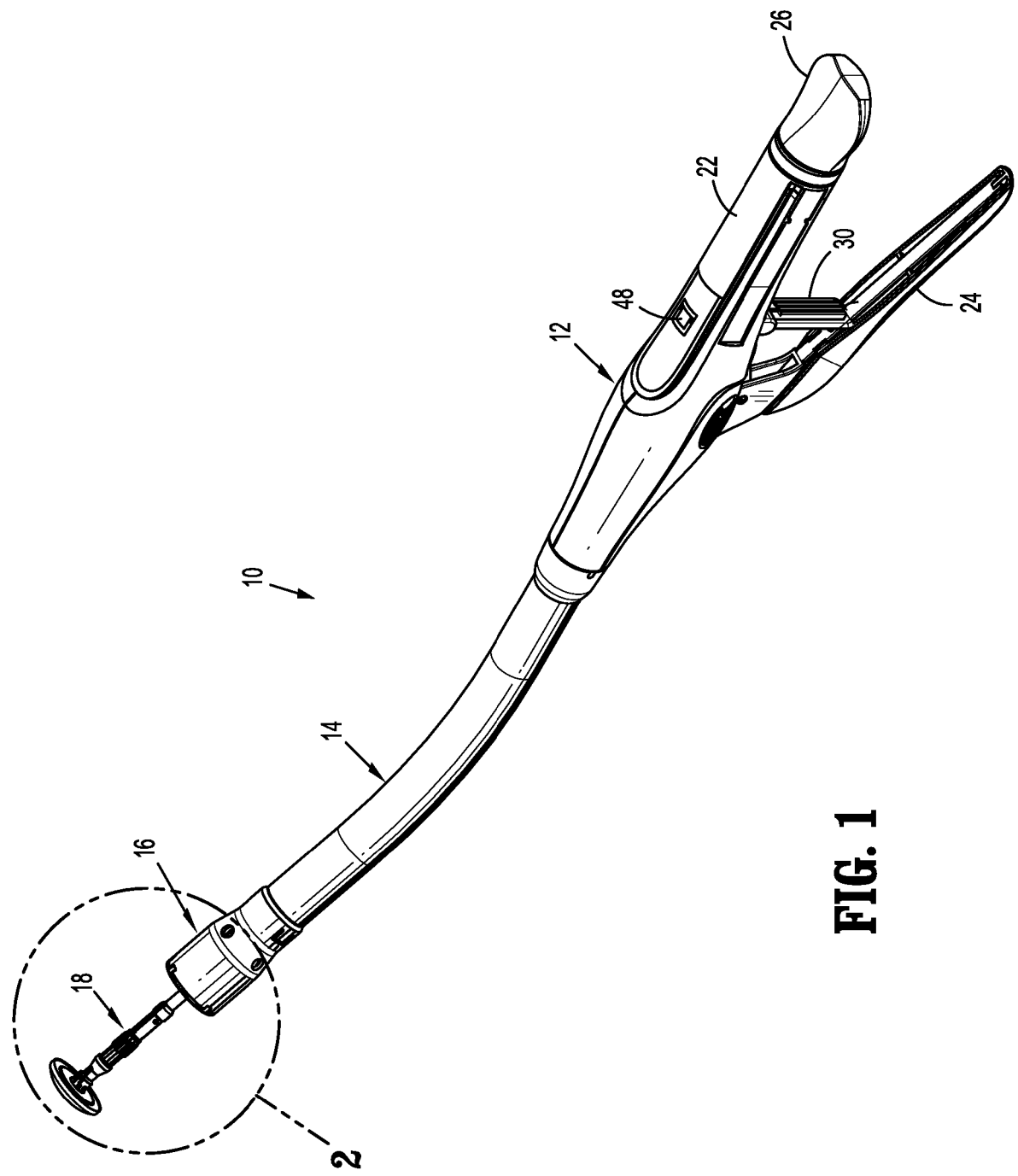
FIG. 1 is a perspective view of a surgical stapler with one embodiment of the presently disclosed tissue gap indicator assembly.

The presently disclosed surgical stapler will now be described in detail with reference to the drawings in which like reference numerals designate identical or corresponding elements in each of the several views. In this description, the term "proximal" is used generally to refer to the portion of the apparatus that is closer to a clinician, while the term "distal" is used generally to refer to the portion of the apparatus that is farther from the clinician. In addition, the term "endoscopic" is used generally to refer to endoscopic, laparoscopic, arthroscopic, and any other surgical procedure performed through a small incision or a cannula inserted into a patient's body. Finally, the term clinician is used generally to refer to medical personnel including doctors, nurses, and support personnel.

The presently disclosed surgical stapler includes a handle assembly supporting an indicator assembly that includes an indicator slide and an indicator lever. The handle assembly defines a window that allows for visualization of the indicator slide. The indicator slide has indicia that is visible through the window in the handle assembly. The indicator lever is operatively engaged with the indicator slide to effect movement of the indicator slide from a non-actuated position within the handle assembly to an actuated position within the handle assembly. As the indicator slide moves between the non-actuated position and the actuated position, the indicia on the indicator slide moves beneath the window and provides an indication to a clinician as to the existing tissue gap defined between an anvil assembly and a cartridge assembly and whether the anvil and cartridge assemblies are in a fire-ready zone. In the presently disclosed indicator assembly, the indictor lever interconnects the indicator lever and a drive screw and amplifies to provide movement of the indicator slide to allow a clinician to more easily visualize approximation of the anvil and cartridge assemblies within the firing zone.

FIG. 1 illustrates one embodiment of the presently disclosed surgical stapler 10. Briefly, surgical stapler 10 includes a handle assembly 12, a central body or elongated portion 14, a shell or cartridge assembly 16, and an anvil assembly 18. Although the central body portion 14 is shown to be slightly curved, it is to be understood that the central body portion 14 can be straight or have any degree of curvature suitable to perform a desired surgical procedure.

Except where otherwise noted, the components of stapler 10 are generally formed from thermoplastics including polycarbonates, and metals including stainless steel and aluminum. The particular material selected to form a particular component will depend upon the strength requirements of the particular component and upon whether the component is a reusable or disposable component. For example, the anvil may be formed from a metal such as stainless steel, whereas portions of handle assembly 12 may be formed from thermoplastic such as a polycarbonate. In addition, the handle assembly 12 may be formed of an autoclavable material to allow for reuse whereas portions of the cartridge assembly may be formed of thermoplastics to allow for disposal. It is envisioned that other materials having the requisite strength requirements which are suitable for surgical use may be used to form the components of surgical stapler 10.

Handle assembly 12 includes a stationary handle 22, a firing trigger 24, an approximation knob 26, an indicator assembly 28, and a lockout mechanism 30. The approximation knob 26 functions to retract and advance a drive screw 40 (FIG. 3) to advance or retract the anvil assembly 18 in relation to the cartridge assembly 16 between spaced and approximated positions. The lockout mechanism 30 functions to prevent actuation of the firing trigger 24 until the anvil assembly 18 and the cartridge assembly 16 have been approximated into a firing zone, i.e., a position in which the tissue gap between the anvil and cartridge assemblies is reduced to allow for proper formation of staples. The firing trigger 24 functions to actuate a pusher (not shown) to eject staples from cartridge assembly 16 after the cartridge and anvil assemblies 16 and 18, respectively have been approximated within the firing zone.

Each of the components of handle assembly 12 identified above are substantially as described in U.S. Pat. No. 7,303,106 ("'106 patent") entitled "Surgical Stapling Device With Visual Indicator" which issued on Dec. 4, 2007. The '106 patent is incorporated herein by reference in its entirety. Accordingly, only those components of the handle assembly 12 that interact with the presently disclosed indicator assembly will be described in further detail herein. The remaining components and assemblies will not be described in further detail herein.

Figure 2:
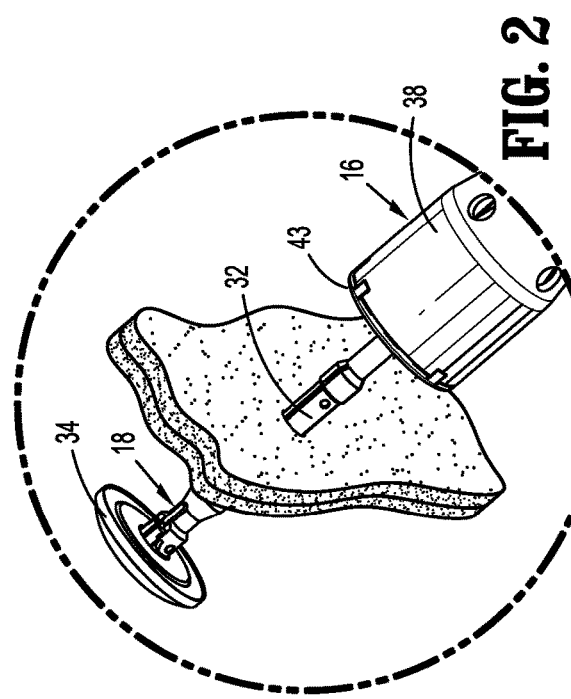
FIG. 2 is an enlarged view of the area of detail of FIG. 1.

Referring to FIG. 2, the anvil assembly 18 includes an anvil shaft or center rod 32 and an anvil head 34. In embodiments, the anvil head 34 is fixedly mounted to a distal end of anvil shaft 32. Alternatively, the anvil head 34 may be pivotally mounted to the distal end of anvil shaft 32 such that the anvil head 34 can move between an operative non-tilted position to a tilted position (not shown). This is described in detail in the '106 patent.

The cartridge assembly 16 is secured to the distal end of central body portion 14 of the surgical stapler 10 and includes a shell or housing 38. The housing 38 supports a pusher (not shown), a knife (not shown), and a staple guide 43 housing one or more rows of staples. Details of the components of the cartridge assembly 16 are provided in the '106 patent which is incorporated herein by reference in its entirety.

Figure 3:
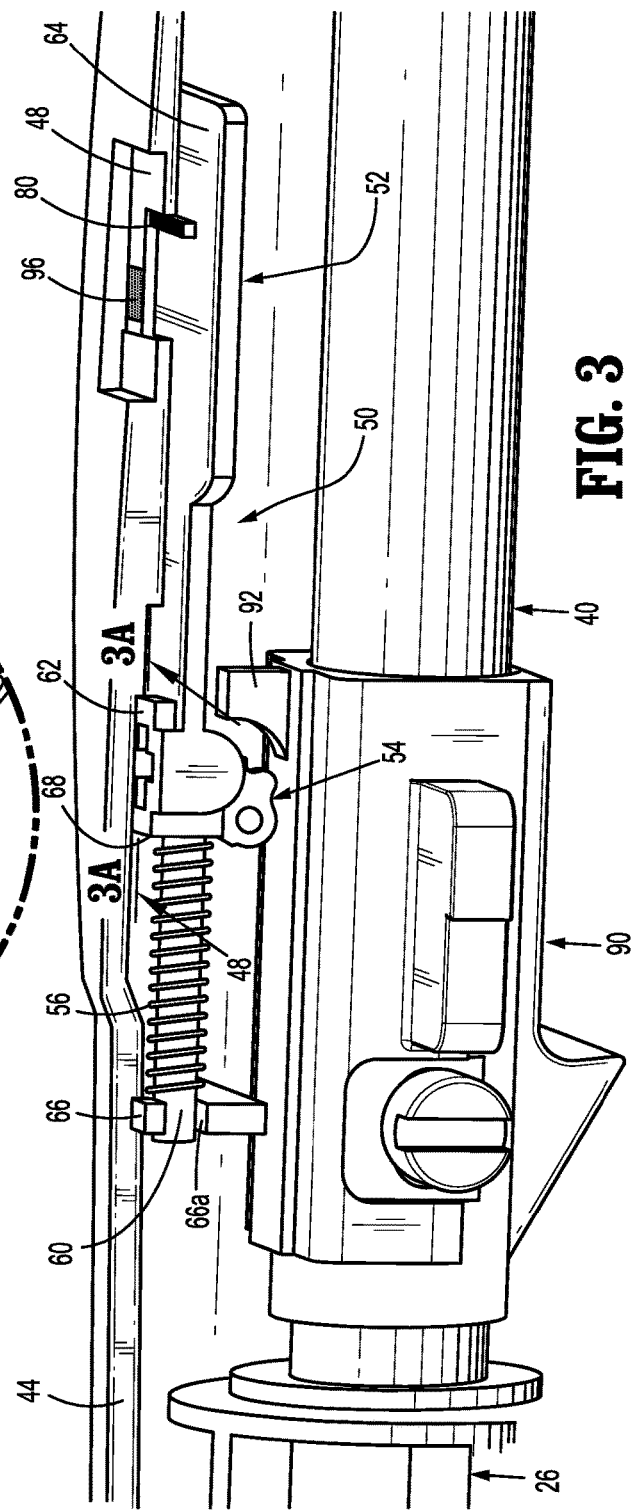
FIG. 3 is a side perspective view of the stationary handle of the surgical stapler shown in FIG. 1 with a body half-section removed to expose the screw stop and tissue gap indicator assembly.

Referring to FIGS. 3 and 3A, the stationary handle 22 of the handle assembly 12 includes a housing 44 that defines a window 48 and supports a tissue gap indicator assembly 50. The tissue gap indicator assembly 50 includes a slide 52, a lever 54, and a biasing member 56. The slide 52 includes a proximal portion 60, a central portion 62, and a distal portion 64. The proximal portion 60 of the slide 52 is supported within a cutout 66a of a bracket 66 that is fixedly secured to an inner wall of the housing 44 of the stationary handle 22. The central portion 62 defines a proximal shoulder 68, a channel 70 that receives the lever 54 as discussed in detail below, and a vertical groove 72. The biasing member 56 is positioned between the bracket 66 and the proximal shoulder 68 of the central portion 62 of the slide 52 to urge the slide 52 in a distal direction to an unactuated position. The distal portion 64 of the slide 52 supports indicia 80 which is positioned beneath the window 48 of the housing 44 of the stationary handle 22. In embodiments, the indicia 80 may include a colored line, e.g., a black line. In some embodiments, the indicia 80 may include a raised protrusion that extends at least partly into the window 48. The raised protrusion may be linear and colored, e.g., a raised black line. The slide 52 is movable from a distal position in which the indicia 80 is positioned at the distal end of the window 48 to a proximal position in which the indicia 80 is positioned at the proximal end of the window 48 as described in detail below.

As discussed above, the lever 54 is supported in the channel 70 of the central portion 62 of the slide 52. The lower portion of the lever 54 is pivotally supported within the housing 44 of the stationary handle 22 by a post 82. The upper portion of the lever 54 supports a pair of radially extending protrusions 84 that are received within the vertical grooves 72 defined in the outer walls defining the channel 70 and spaced from the post 82. The vertical grooves 72 allow for rotatable or pivotal movement of the lever 54 to facilitate longitudinal movement of the slide 52. The lever 54 also defines an engagement surface 86 that is positioned near to the post 82. In embodiments, the engagement surface 86 includes two engagement members 86a and 86b which are described in detail below.

As described above, the approximation knob 26 functions to retract and advance a drive screw 40 to advance or retract the anvil assembly 18 in relation to the cartridge assembly 16 between spaced and approximated positions. A screw stop 90 is fixedly supported on the drive screw 40. The screw stop 90 includes an abutment 92 that is positioned to engage the engagement surface 86 of the lever 54 when the drive screw 40 is moved from an advanced position towards a retracted position to move the anvil assembly 18 and the cartridge assembly 16 from the spaced position towards the approximated position. The abutment 92 has a curved engagement surface 92a that allows the abutment 92 to transition between the first and second engagement members 86a and 86b of the lever 54 as the abutment 92 pivots the lever 54 about the post 82.

Referring also to FIGS. 4 and 4A, when the anvil assembly 18 and cartridge assembly 16 are in a spaced position, the abutment 92 is positioned distally of the engagement surface 86 of the lever 54. In this position, the biasing member 56 of the indicator assembly 50 urges the slide 52 distally to position the indicia 80 in the distal end of the window 48. Since the protrusions 84 on the lever 54 are received in the vertical grooves 72 of the central portion 62 of the slide 52, when the slide is urged to its distal-most or unactuated position, the lever 54 is pivoted in a clockwise direction to the position viewed in FIG. 3.

As shown in FIG. 3, outer edges of the housing 44 of the stationary housing 22 defining the window 48 may include indicia 96. Indicia 96 is positioned to align with the indicia 80 to indicate to a clinician when the anvil assembly 18 and cartridge assembly 16 are in a fire-ready zone, i.e., the zone in which the cartridge and anvil assemblies 16, 18, respectively, are approximated sufficiently to facilitate the proper formation of staples. The indicia 96 on the housing 44 may include a colored band 96a that is positioned to align with the indicia 80. When the indicia 80 is moved to a position within the band 96a, an indication is provided to the clinician that the cartridge and anvil assemblies 16, 18 are sufficiently approximated and are in the fire-ready zone.

Figure 5A:
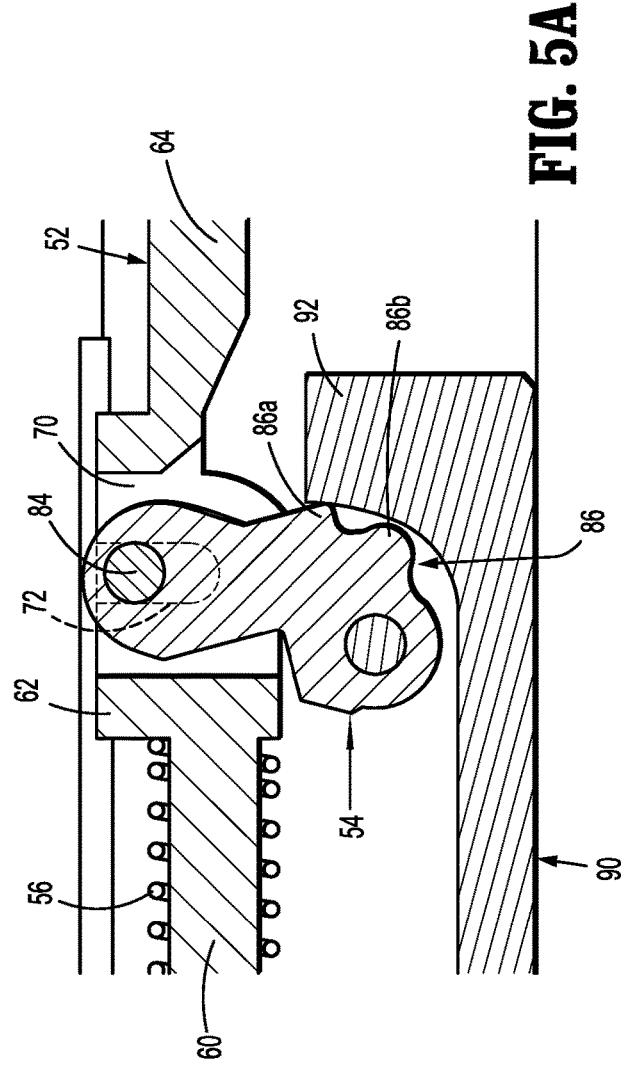
FIG. 5A is a side cross-sectional, cutaway view of the indicator lever and indicator slide of the indicator assembly shown in FIG. 3 after approximation of the cartridge and anvil assemblies into the maximum tissue gap position of the fire-ready zone.

Referring to FIGS. 5 and 5A, when the drive screw 40 is retracted to begin approximation of the cartridge and anvil assemblies 16, 18 (FIG. 1), the abutment 92 of the screw stop 90 moves towards and engages the first engagement member 86a of the engagement surface 86 of the lever 54 to initiate pivotal movement of the lever 54 about the post 82 in a counter-clockwise direction as viewed in FIG. 5A. As the lever 54 pivots, the protrusions 86 of the lever 54 that are received in the vertical grooves 72, engage the walls defining the vertical grooves 72 to move the slide 52 longitudinally in a proximal direction to move the indicia 80 within the window 48. As shown in FIG. 5, when a predetermined degree of approximation is reached, the indicia 80 will become aligned with a proximal end of the band 96a to indicate to a clinician that the cartridge and anvil assemblies 16, 18 have reached a maximum gap position within the fire-ready zone.

Figure 6:
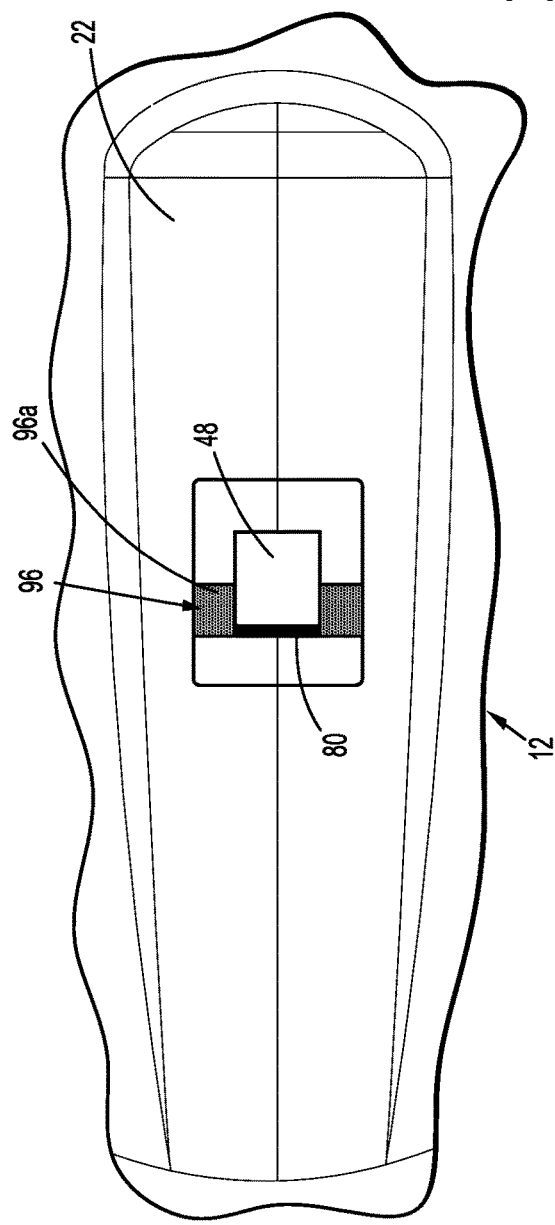
FIG. 6 is a top view of the stationary handle of the surgical stapler shown in FIG. 1 illustrating the surgical stapler in a minimum tissue gap position of the fire-ready zone.

Referring to FIGS. 6 and 6A, as the drive screw 40 is retracted further to move the cartridge and anvil assemblies 16, 18 towards the fully approximated position, the lever 54 continues to pivot in a counter-clockwise direction as viewed in FIG. 6A. At some point in time during approximation of the cartridge and anvil assemblies 16, 18, the abutment 92 on the screw stop 90 will disengage from the first engagement member 86a of the lever 54 and move into engagement with the second engagement member 86b of the lever 54 to continue pivotal movement of the lever 54. As the lever 54 is pivoted, the protrusions 84 on the lever 54 that are received in the vertical grooves 72 of the central portion 62 of the slide 52 continue to urge the slide 52 proximally against the force of the biasing member 56 to move the indicia 80 to the proximal end of the window 46 of the stationary housing 22. As shown in FIG. 5, when the cartridge and anvil assemblies 16 and 18 are fully approximated, the indicia 80 will become aligned with a distal end of the band 96a to indicate to a clinician that the cartridge and anvil assemblies 16, 18 have reached a minimum gap position within the fire-ready zone.

Referring to FIG. 6A, the radii R1 and R1' defined between the central axis of the post 82 and the engagement surfaces 86a and 86b, respectively, of the lever 54 is substantially smaller than the radius R2 defined between the central axis of the post 82 and the protrusions 84. As such, as the abutment 92 of the screw stop 90 is moved a longitudinal distance of X1 to pivot the lever 54 about the axis defined by the post 82, pivotal movement of the lever 54 will effect longitudinal movement of the slide 52 over a greater distance X2. By providing a lever 54 that has engagement members 86a and 86b spaced closer to the pivot axis of the lever 54 than the protrusions 84 that drive the slide 52, the longitudinal movement of the slide 52 effected by the longitudinal movement of the abutment 92 of the screw stop 90 and drive screw 40 will be multiplied by a factor of R2/R1 or R2/R1' to allow for a larger distance of movement of the indicia 80 within the window 48 as the cartridge and anvil assemblies 16, 18 are approximated through the fire-ready zone. This allows a clinician to better visualize the progression of approximation of the cartridge and anvil assemblies through the fire-ready zone.

Referring to FIG. 7, when the drive screw 40 is moved distally to move the cartridge and anvil assemblies 16, 18 from the approximated position to the spaced position, the abutment 92 of the screw stop 90 moves distally with the drive screw 40 and moves away from the lever 54. As the abutment 92 moves distally away from the lever 54, the biasing spring 56 urges the slide 52 distally. As discussed above, when the slide 52 moves distally, the lever 54, with the protrusions 84 received in the vertical grooves 72 of the slide 52, is pivoted in a clockwise direction as viewed in FIG. 7. Distal movement of the slide 52 effects movement of the indicia 80 back to the distal end of the window 48.

Figure 8:
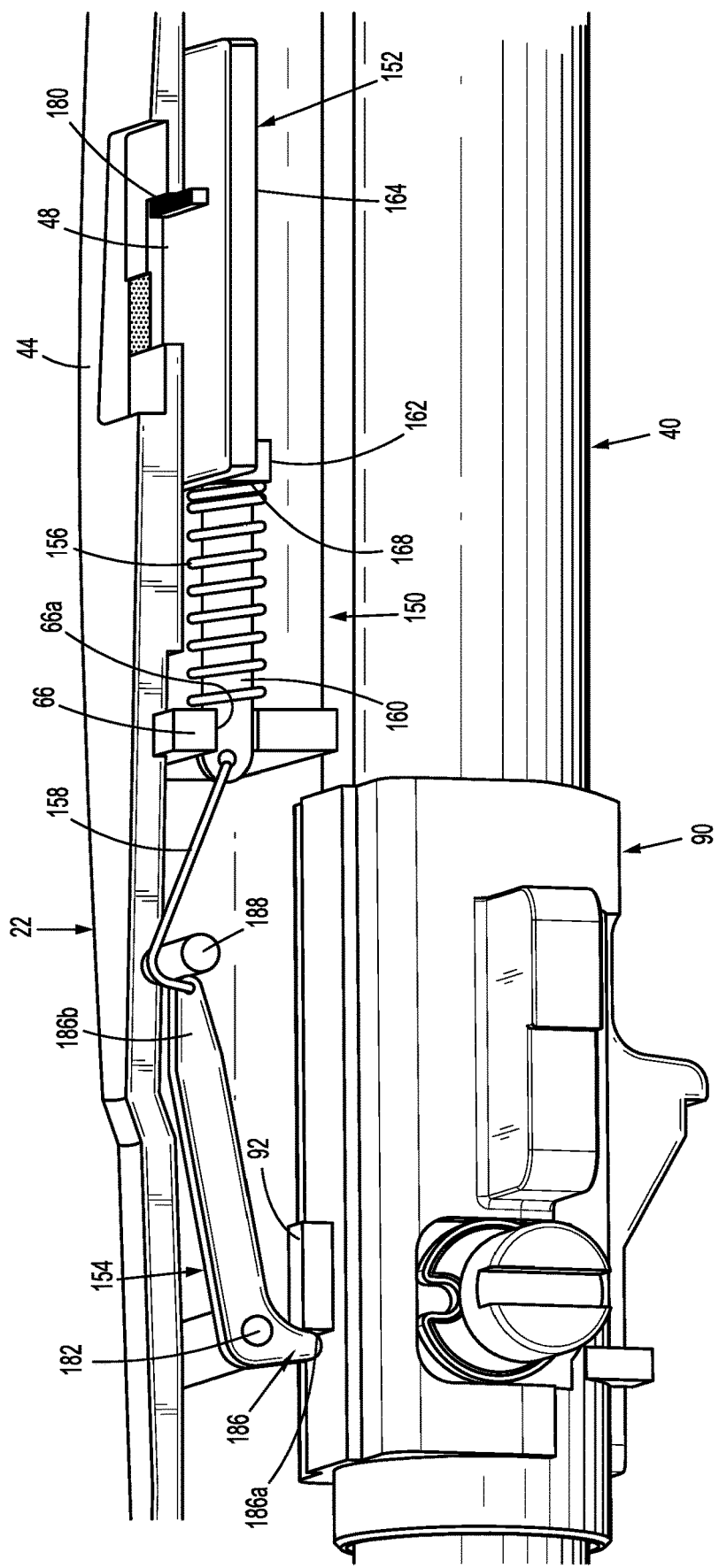
FIG. 8 is a side perspective view of another embodiment of the presently disclosed surgical stapler with a tissue gap indicator assembly.

FIG. 8 illustrates an alternative embodiment of the presently disclosed tissue gap indicator assembly for multiplying the distance of movement of the slide shown generally as 150. Indicator assembly 150 includes a slide 152, a lever 154, a biasing member 156, and a link 158. In embodiments, the link is a non-rigid member, e.g., string, rope, cable, or the like. The slide 152 has a proximal portion 160 that extends through the cutout 66a formed in the bracket 66, a central portion 162 defining a shoulder 168, and a distal portion 164 that supports indicia 180 which is positioned beneath the window 48 of the housing 44 of the stationary handle 22. The lever 154 is pivotally supported about a post 182 supported within the housing 44 of the stationary handle 22 and includes a first end 186 having an engagement member 186a and a second end 186b secured to a proximal end of the link 158. The link 158 extends over a support post 188 that is fixedly supported within the housing 44 of the stationary handle 22 and has a distal end secured to a proximal end of the proximal portion 160 of the slide 152. The biasing member 156 is positioned about the proximal portion 160 of the slide 152 between the shoulder 168 and the bracket 66 to urge the slide 152 distally within the stationary handle 22.

In use, when the drive screw 40 is retracted to approximate the cartridge and anvil assemblies 16, 18 (FIG. 1), the abutment 92 of the screw stop 90 moves toward and engages the engagement member 186a of the lever 154 to initiate pivotal movement of the lever 154 about the post 182 in a clockwise direction as viewed in FIG. 8. As the lever 154 pivots about the post 182, the link 158 is pulled downwardly over the support post 188 to pull the slide 152 longitudinally in a proximal direction to move the indicia 180 proximally within the window 48. As illustrated, the distance between the pivot axis of the lever 154, and the engagement member 186a of the lever 154 is shorter than the distance between the pivot axis of the lever 152 and the second end 186b of the lever 154 that is secured to a proximal end of the link 158. As such, when the abutment 92 engages the engagement member 186a of the lever 154 and the lever 154 is pivoted about the post 182, longitudinal movement of the slide 152 effected by the pivotal movement of the lever 154 is amplified or multiplied such that the distance of movement of the indicia 180 within the window 48 as the cartridge and anvil assemblies 16, 18 are approximated through the fire-ready zone is greater than the distance of movement of the abutment 92.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical stapler comprising:
   a handle assembly including a stationary handle and a firing trigger, the stationary handle defining a window;
   a central body extending distally from the handle assembly;
   a cartridge assembly supported on a distal end of the central body;
   an anvil assembly supported adjacent the distal end of the central body, the anvil assembly being movable in relation to the cartridge assembly between spaced and approximated positions;
   an approximation mechanism including a drive screw that is longitudinally movable, the drive screw being operatively connected to the anvil assembly such that longitudinal movement of the drive screw effects movement of the anvil assembly in relation to the cartridge assembly between the spaced and approximated positions, the drive screw supporting an abutment; and
   an indicator assembly including a slide and a lever, the slide having indicia visible through the window in the stationary handle, the lever being operatively engaged with the slide and positioned to engage the abutment on the drive screw when the drive screw is moved proximally within the stationary handle to translate longitudinal movement of the drive screw into longitudinal movement of the slide to effect longitudinal movement of the indicia within the window, wherein the lever is engaged with the abutment and is configured to translate movement of the abutment over a distance of X1 into movement of the slide over a distance of X2, wherein X2 is greater than X1.

2. The surgical stapler according to claim 1, wherein the indicator assembly further includes a biasing member, the biasing member being positioned to urge the slide distally within the stationary handle.

3. The surgical stapler according to claim 1, wherein the lever is pivotally mounted within the stationary housing about a post defining a pivot axis, the lever having an engagement surface spaced from the pivot axis of the post by a distance of R1, the engagement surface being positioned to engage the abutment.

4. The surgical stapler according to claim 3, wherein the lever includes a protrusion that is operatively engaged with the slide, the protrusion being spaced from the pivot axis defined by the post by a distance of R2, wherein R2 is greater than R1.

5. The surgical stapler according to claim 1, wherein the lever includes a first engagement member and a second engagement member, the first engagement member being spaced from the pivot axis defined by the post the distance R1 and the second engagement member being spaced from the pivot axis defined by the post a distance R1', wherein the R1' is greater than R1 but less than R2.

6. The surgical stapler according to claim 5, wherein the abutment defines a curved abutment surface.

7. The surgical stapler according to claim 2, wherein the slide has a proximal portion, a central portion, and a distal portion, the central portion defining a channel that receives the lever.

8. The surgical stapler according to claim 7, wherein the central portion of the slide defines a vertical groove and the lever includes a protrusion received within the vertical groove, the protrusion being movable within the vertical groove to facilitate longitudinal movement of the slide when the lever is pivoted.

9. The surgical stapler according to claim 7, wherein the biasing member is positioned about the proximal portion of the slide.

10. The surgical stapler according to claim 7, wherein the indicia is formed on the distal portion of the slide.

11. The surgical stapler according to claim 10, wherein the indicia includes a colored line.

12. The surgical stapler according to claim 11, wherein the stationary handle defines second indicia positioned about the window, the second indicia being associated with the indicia on the slide to identify to a clinician when the cartridge and anvil assemblies are approximated into a fire-ready zone.

13. The surgical stapler according to claim 1, wherein the approximation mechanism includes a rotation knob, the rotation knob being rotatable in relation to the stationary handle to effect longitudinal movement of the drive screw within the stationary handle.

14. The surgical stapler according to claim 1, wherein the indicator assembly further includes a non-rigid link having a first end attached to a distal end of the lever and a second end attached to a proximal end of the slide.

15. The surgical stapler according to claim 14, wherein the non-rigid link is supported on a support post positioned between the distal end of the lever and the proximal end of the slide.

16. The surgical stapler according to claim 14, wherein the lever is pivotally mounted within the stationary handle about a post defining a pivot axis, the lever including a proximal end defining an engagement surface, the post being positioned between the proximal and distal ends of the lever, wherein the engagement surface is positioned a distance of R1 from the pivot axis of the post and the distal end of the lever attached to the non-rigid link is positioned a distance of R2 from the pivot axis of the post, wherein R2 is greater than R1.

17. A surgical stapler comprising:
a handle assembly including a stationary handle and a firing trigger, the stationary handle defining a window;
a central body extending distally from the handle assembly;
a cartridge assembly supported on a distal end of the central body;
an anvil assembly supported adjacent the distal end of the central body, the anvil assembly being movable in relation to the cartridge assembly between spaced and approximated positions;
an approximation mechanism including a longitudinally movable drive screw, the drive screw being operatively connected to the anvil assembly such that longitudinal movement of the drive screw effects movement of the anvil assembly in relation to the cartridge assembly between the spaced and approximated positions, the drive screw supporting an abutment; and
an indicator assembly including a slide and a lever, the slide having indicia visible through the window in the stationary handle and movable along a longitudinal path between advanced and retracted positions, the lever being operatively engaged with the slide and positioned to engage the abutment on the drive screw when the drive screw is moved proximally within the stationary handle to translate longitudinal movement of the drive screw into longitudinal movement of the slide to effect longitudinal movement of the indicia within the window, wherein the lever is engaged with the abutment and is configured to translate movement of the abutment over a distance of X1 into movement of the slide over a distance of X2, wherein X2 is greater than X1.

18. A surgical stapler comprising:
a handle assembly including a stationary handle and a firing trigger, the stationary handle defining a window;
a central body extending distally from the handle assembly;
a cartridge assembly supported on a distal end of the central body;
an anvil assembly supported adjacent the distal end of the central body, the anvil assembly being movable in relation to the cartridge assembly between spaced and approximated positions;
an approximation mechanism including a longitudinally movable drive screw, the drive screw being operatively connected to the anvil assembly such that longitudinal movement of the drive screw effects movement of the anvil assembly in relation to the cartridge assembly between the spaced and approximated positions, the drive screw supporting an abutment; and
an indicator assembly including a slide and a lever, the slide having indicia visible through the window in the stationary handle, the lever being operatively engaged with the slide and positioned to engage the abutment on the drive screw when the drive screw is moved proximally within the stationary handle to translate longitudinal movement of the drive screw into longitudinal movement of the slide to effect longitudinal movement of the indicia within the window, wherein the lever is engaged with the abutment and is configured to translate movement of the abutment over a distance of X1 into movement of the slide over a distance of X2, wherein X2 is greater than X1, the lever configured to change the rate of longitudinal movement of the slide as the slide moves along a longitudinal path between advanced and retracted positions.

* * * * *